US00PP31466P2

(12) United States Plant Patent
Korlipara

(10) Patent No.: US PP31,466 P2
(45) Date of Patent: Feb. 18, 2020

(54) ***ECHINACEA* PLANT NAMED 'EMBERS FEVER'**

(50) Latin Name: ***Echinacea* spp.**
Varietal Denomination: Embers Fever

(71) Applicant: Terra Nova Nurseries, Inc., Canby, OR (US)

(72) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 16/501,660

(22) Filed: May 17, 2019

(51) Int. Cl.
*A01H 5/02* (2018.01)
*A01H 6/14* (2018.01)

(52) U.S. Cl.
USPC ..... Plt./428

(58) Field of Classification Search
USPC ..... Plt./428
CPC ..... A01H 5/02; A01H 6/14
See application file for complete search history.

*Primary Examiner* — Annette H Para
(74) *Attorney, Agent, or Firm* — Klarquist Sparkman, LLP

(57) ABSTRACT

A new and distinct *Echinacea* plant named 'Embers Fever' is characterized by an amazing number of inflorescences starting in the first season, deep, crimson red ray florets surrounding dark cones, long bloom time with excellent rebloom, excellent branching with large blooms on sturdy stems, and excellent vigor.

1 Drawing Sheet

Botanical denomination: *Echinacea* spp.
Variety designation: 'Embers Fever'.

BACKGROUND OF THE INVENTION

The present invention relates to a new and distinct cultivar of *Echinacea* given the cultivar name 'Embers Fever'. *Echinacea* is in the family Asteraceae. The exact parents of this selection are unknown, unnamed, proprietary interspecific hybrids bred from *Echinacea paradoxa, Echinacea purpurea,* and *Echinacea tennesseensis*. The new cultivar is part of a planned breeding program for container grown, well branched, compact, bright, long lasting flower color, and extended bloom time.

Compared to *Echinacea* 'TNECHKRD' (trade designation KISMET® Red'), U.S. Plant Pat. No. 29,743, the new cultivar is taller with deeper, blue-red ray florets. Compared to *Echinacea* PRIMA™ Ruby ('TNECHPR'), U.S. Plant Pat. No. 30,204, the new cultivar is taller, more open in habit, and a deeper red.

SUMMARY OF THE INVENTION

The present invention has not been evaluated under all possible environmental conditions. The phenotype may vary with variations in environment without a change in the genotype of the plant.

*Echinacea* 'Embers Fever' is uniquely distinguished by:

1. an amazing number of inflorescences starting in the first season,
2. deep, crimson red ray florets surrounding dark cones,
3. long bloom time with excellent rebloom,
4. excellent branching with large blooms on sturdy stems, and
5. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a close up of the inflorescences of *Echinacea* 'Embers Fever' on an eight-month-old plant growing in the trial field in full sun in mid-September in Canby, Oreg.

DETAILED PLANT DESCRIPTION

The following is a detailed description of the new *Echinacea* cultivar based on observations of nine-month-old specimens growing in the trial field under full sun, during mid-September in Canby, Oreg. Canby is in Zone 8 on the USDA Hardiness map. Temperatures range from a high of 95 degrees F. in August to an average of 32 degrees F. in January. Normal rainfall is 42.8 inches per year in the trial fields in Canby, Oreg. The color descriptions are all based on The *Royal Horticultural Society Colour Chart,* 5$^{th}$ edition, 2007.

Plant:

*Type*.—Herbaceous perennial.
*Hardiness*.—USDA Zones 4 to 9.
*Size*.—Grows to about 53 cm wide and 56 cm tall to top of inflorescences.
*Form*.—Basal clump, with up to 9 crowns.
*Vigor*.—Excellent.

*Roots*.—Fibrous, with many downward growing and few laterals, ivory in color.

Leaf (basal):

*Type*.—Simple.

*Shape*.—Lanceolate.

*Arrangement*.—Alternate.

*Leaf number*.—30.

*Blade size*.—Grows to 18 cm long and 4.7 cm wide.

*Margins*.—Sparsely serrate.

*Apex*.—Acuminate.

*Base*.—Attenuate.

*Surface texture*.—Both sides strigose.

*Venation*.—Pinnate.

*Variegation*.—Absent.

*Color*.—Between Green N137 and Green 137A with veins Green 145C on topside, Green 147B with veins Green 147C on bottom side; petiole clasping, to 8 cm long and 3 mm wide, strigose, Green 147C Yellow White 158D, roots develop easily from cuttings from the crown.

Leaf (stem):

*Type*.—Simple.

*Shape*.—Lanceolate.

*Arrangement*.—Alternate.

*Leaf number*.—Up to 45 on a single, branched, main stem.

*Blade size*.—Grows to 15 cm long and 4.1 cm wide.

*Margins*.—Entire.

*Apex*.—Acuminate.

*Base*.—Attenuate.

*Surface texture*.—Strigose on both sides.

*Venation*.—Pinnate, Yellow Green 147C on both sides.

*Color*.—Topside between Yellow Green 147A and Green 139A, bottom side Green 137B.

*Petiole description*.—Clasping, grows to 6.3 cm long and 4 mm wide, scabrous, narrow leafy edges which fold upwards, topside Green 137C in middle with leafy Green N137B edges, bottom side closest to Yellow Green 147B.

Inflorescence:

*Type*.—Composite on terminal stalked heads.

*Number of fully expanded flowers*.—Up to 60.

*Flowering stem*.—Grows to 23 cm tall from the base of the plant to the terminal leaves below the peduncle; unbranched to branched, 2 to 4 inflorescences per stem; diameter growing to 9 mm wide near the inflorescence; strigose, strong; Yellow Green 146C tinted Greyed Orange 166A in sun.

*Size*.—Grows to 9.5 cm wide and 5 cm deep as disc enlarges.

*Form*.—Ray florets held horizontally, mature disc is conic.

*Peduncle*.—Grows to 29 cm long from above terminal leaves to flower, 4 cm wide, strigose; Yellow Green 146C.

*Peduncle strength*.—Strong.

*Immature inflorescence* (*bud*).—Up to 25, 3.8 cm wide and 2.5 cm deep, ray florets held upright at a 50 degree angle and rolled up so only the back color shows, Red Purple 59B blending to Yellow Green 146C on top 3 mm, disc color closest to Green 137C in center.

*Ray florets*.—Without pistil or stamen, 21 to 30 in number, grow to 43 mm long and 12 mm wide, oblanceolate with the tip two-to three-toothed (each acute), entire margins, base attenuate, glabrous on both sides; topside closest to Red 53A, bottom side Red Purple 60A; aging to (when disc florets fully open) topside Red 53A tinted Red 53D.

*Disc*.—Flat becoming conic, becoming 25 mm deep and 35 mm wide with maturity, Greyed Purple 187B in background with bracts Greyed Purple 185A with tips Greyed Purple 187A.

*Disc florets*.—To about 520 in number, each with 1 pistil and 4 stamens, grow to 8 mm long and 2.5 mm wide, each with one persistent, very stiff linear bract (14 mm long with the tip Greyed Purple 187A to 4 mm Greyed Purple N186D blending to 4 mm Yellow Green 147C blending to White NN155A on bottom); corolla 12 mm long and 3 mm wide, tubular, 5 lobed, glabrous, Greyed Purple 187B with lobe tips 187A; pistil 11 mm long, ovary 4 mm long, White NN155D with top Yellow Green 144A, style 5 mm long White NN155A, 2-branched stigma spreading 2.5 mm wide, Greyed Purple 187A; stamen 4.5 mm long, filaments 2 mm long and White NN155B, anthers 2 mm long and Greyed Brown N199A, pollen slight, Yellow Orange 16A.

*Involucral bracts*.—In 4 leafy series, area grows to 43 mm wide and 8 mm deep, lobes lanceolate in shape, reflexed, grow to 11 mm long and 3 mm wide, Green N137A, margins strigose, tip acute, strigose on both sides.

*Receptacle*.—Grows to 8 mm wide and 15 mm deep, White NN155B.

*Bloom period*.—June through October in Canby, Oreg.

*Fragrance*.—Floral, sweet.

*Lastingness*.—Each inflorescence lasts about four weeks in Canby, Oreg.

*Seeds*.—3 mm long and 2.5 mm wide, oval, Brown 200C.

*Fertility*.—Moderate.

Disease and pests: No pests or diseases have been observed on plants grown under commercial conditions in Canby, Oreg. No resistances are known.

I claim:

1. A new and distinct *Echinacea* plant as herein illustrated and described.

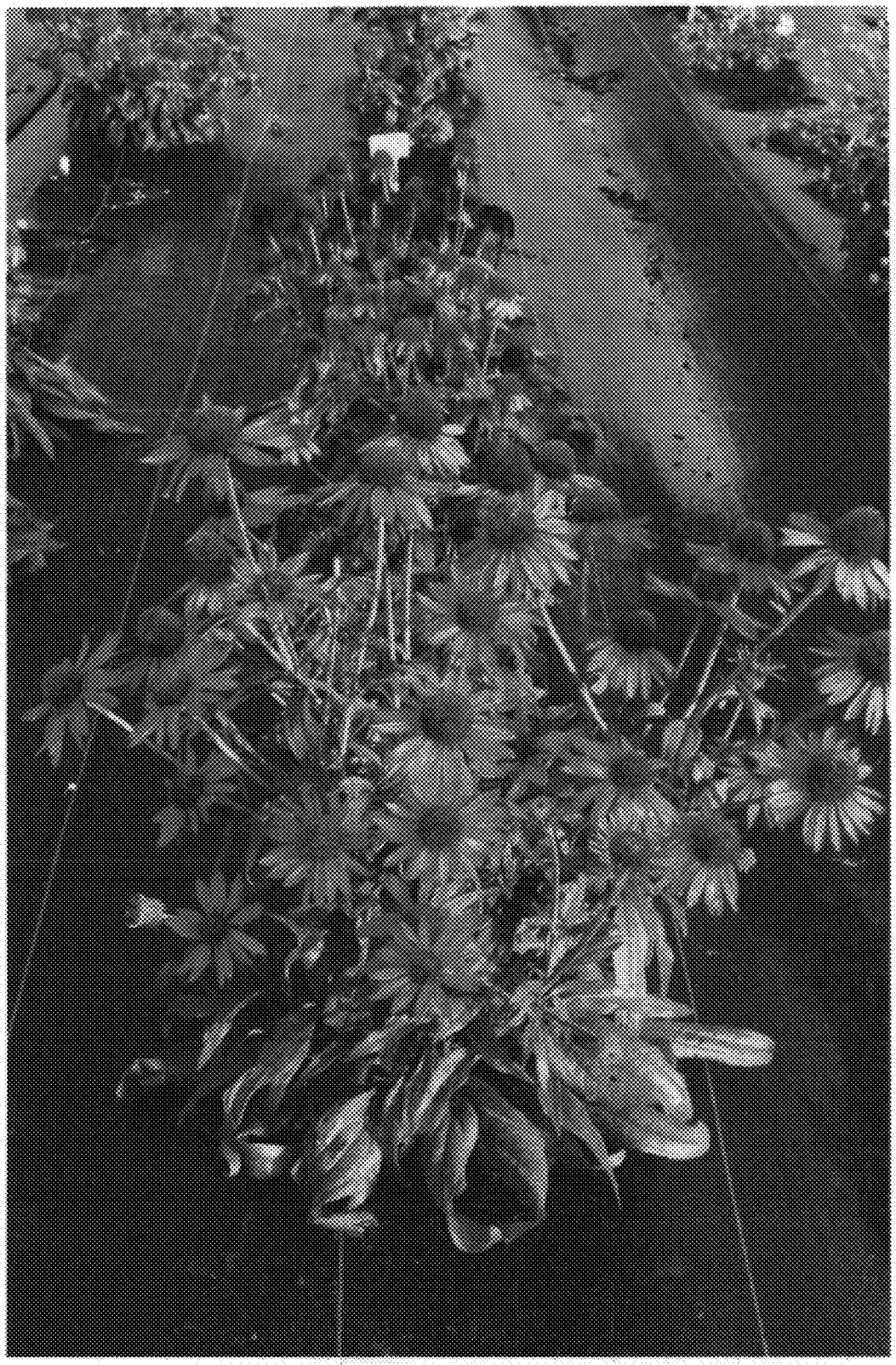

* * * * *